(12) United States Patent
Farha et al.

(10) Patent No.: US 10,479,758 B2
(45) Date of Patent: *Nov. 19, 2019

(54) HAFNIUM-BASED METAL-ORGANIC FRAMEWORKS AS EPOXIDE RING-OPENING CATALYSTS

(71) Applicant: Northwestern University, Evanston, IL (US)

(72) Inventors: Omar K. Farha, Glenview, IL (US); Joseph T. Hupp, Northfield, IL (US); M. Hassan Beyzavi, Evanston, IL (US); Casey J. Stephenson, Evanston, IL (US); Yangyang Liu, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/256,141

(22) Filed: Jan. 24, 2019

(65) Prior Publication Data

US 2019/0152897 A1  May 23, 2019

Related U.S. Application Data

(62) Division of application No. 15/527,605, filed as application No. PCT/US2015/061475 on Nov. 19, 2015, now Pat. No. 10,233,145.

(60) Provisional application No. 62/082,283, filed on Nov. 20, 2014.

(51) Int. Cl.
| | | |
|---|---|---|
| *C07C 247/06* | (2006.01) | |
| *B01J 31/16* | (2006.01) | |
| *C07C 29/159* | (2006.01) | |
| *B01J 31/22* | (2006.01) | |
| *C07F 7/00* | (2006.01) | |
| *C07F 19/00* | (2006.01) | |

(52) U.S. Cl.
CPC .......... *C07C 247/06* (2013.01); *B01J 31/16* (2013.01); *B01J 31/1691* (2013.01); *B01J 31/223* (2013.01); *C07C 29/159* (2013.01); *C07F 7/003* (2013.01); *C07F 19/005* (2013.01); *B01J 2231/48* (2013.01); *B01J 2531/0216* (2013.01); *B01J 2531/48* (2013.01); *B01J 2531/49* (2013.01); *Y02P 20/52* (2015.11)

(58) Field of Classification Search
CPC .... C07C 247/06; C07C 29/159; C07F 19/005
See application file for complete search history.

(56) References Cited

U.S. PATENT DOCUMENTS 9,562,118 B2 * 2/2017 Farha .................. C08F 10/14

OTHER PUBLICATIONS

Benzavi; Journal of the American Chemical Society, Oct. 30, 2014 (e-pub), vol. 136, No. 45. pp. 15861-15864.*

* cited by examiner

*Primary Examiner* — Pancham Bakshi
(74) *Attorney, Agent, or Firm* — Bell & Manninng, LLC

(57) ABSTRACT

Metal-organic frameworks (MOFs) having inorganic nodes that comprise an octahedral $Hf_6$ cluster capped by eight $\mu_3$-ligands and having twelve octahedral edges, wherein the $\mu_3$-ligands are hydroxo ligands, oxo ligands or aquo ligands; and organic linkers connecting the organic nodes, the organic linkers comprising 1,3,6,8-tetrakis(p-benzoic acid) pyrene units; wherein eight of the twelve octahedral edges of the inorganic nodes are connected to the 1,3,6,8-tetrakis(p-benzoic acid)pyrene units are provided.

2 Claims, 4 Drawing Sheets

HAFNIUM-BASED METAL-ORGANIC FRAMEWORKS AS EPOXIDE RING-OPENING CATALYSTS

CROSS-REFERENCE TO RELATED APPLICATIONS

The present application is a divisional of U.S. patent application Ser. No. 15/527,605 that was filed May 17, 2017, which is the National Stage Entry of under 35 U.S.C. 371 of PCT/US2015/061475, filed Nov. 19, 2015, United States; which claims priority to U.S. provisional patent application No. 62/082,283, filed Nov. 20, 2014; the entire contents of each of which are hereby incorporated herein by reference.

BACKGROUND

Catalyst-mediated reactions of carbon dioxide represent one potential positive contributor to climate-relevant carbon capture and storage/sequestration (CCS). Well-designed reactions that utilize waste $CO_2$ in the production of commercially relevant chemicals are much sought after. Some of these reactions include the formation of carbonates, where the carbonyl carbon obtained from $CO_2$ is isohypsic with its starting material and does not require reagent driven oxidation state changes. The acid catalyzed cycloaddition of $CO_2$ with an epoxide to form a cyclic carbonate, a functionality having various important applications, is a highly atom-economical reaction. Mechanistically, this reaction is based on an acid catalyst that activates the epoxide, which can then be attacked by a nucleophile co-catalyst to form an alkoxide. This intermediate can then react with carbon dioxide to give ultimately the cyclic carbonate. However, on account of the relatively inert nature and low reactivity of $CO_2$, its activation and incorporation into organic substrates still remains a formidable challenge.

Although some homogeneous and several types of heterogeneous catalysts, such as zeolites, silica-supported salts, metal oxides, titanosilicate, a microporous polymer and an organic network have been utilized for the synthesis of cyclic carbonates, most of the processes demand high pressures and temperatures, thus requiring high energy and capital costs.

Ring-opening of epoxides with hydrides is one of the most fundamental reactions in organic chemistry and generally proceeds via an $S_N2$ type mechanism. In the case of asymmetric molecules, hydride attack typically occurs at the most sterically accessible site to form the Markovnikov product. Anti-Markovnikov products of epoxide ring-opening, such as primary alcohols, are critical to the chemical and pharmaceutical industry and significant effort has gone into developing reagents and methodologies to obtain regioselective products. With metal hydrides, Lewis acids such as transition-metals, $AlCl_3$, or $BH_3$ are added to the reaction to shift regioselectivity to the anti-Markovnikov product. While extremely effective, these reagents are added in stoichiometric amounts and, in most cases, lack functional-group tolerance.

SUMMARY

Metal-organic frameworks (MOFs) and method of using the MOFs to catalyze reactions involving an epoxide ring-opening mechanism are provided.

One embodiment of a MOF is a polyoxohafnium cluster based MOF comprising: inorganic nodes that comprise an octahedral $Hf_6$ cluster capped by eight $\mu_3$-ligands and having twelve octahedral edges, wherein the $\mu_3$-ligands are hydroxo ligands, oxo ligands or aquo ligands; and organic linkers connecting the inorganic nodes, the organic linkers comprising 1,3,6,8-tetrakis(p-benzoic acid)pyrene units; wherein eight of the twelve octahedral edges of the inorganic nodes are connected to the 1,3,6,8-tetrakis(p-benzoic acid) pyrene units. These MOFs and their isostructural polyoxozirconium cluster based MOFs can be used to catalyze reactions of epoxide group-containing molecules that involve an epoxide ring opening step.

One embodiment of a method of catalyzing a reaction using the MOFs comprises combining an epoxide ring-containing molecule with a reactant in the presence of a catalytic amount of the MOF in a solution, wherein the MOF catalyzes a nucleophilic epoxide ring opening of the epoxide ring-containing molecule to provide an activated epoxide and the activated epoxide reacts with the reactant to form a product molecule.

In some of the embodiments of the methods, the MOFs are used to catalyze the formation of cyclic carbonates from carbon dioxide. In other embodiments of the methods, the MOFs are used to catalyze the regioselective and enantioretentive synthesis of 1,2-bifuctionalized systems from reactants such as azides and alcohols. In still other embodiments of the methods, the MOFs are used to catalyze the synthesis of primary alcohols from hydrides.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

DETAILED DESCRIPTION

Metal-organic frameworks (MOFs) and method of using the MOFs to catalyze reactions involving a epoxide ring-opening mechanisms are provided. The MOFs have a porous structure comprising metal nodes, also referred to as centers, coordinated via organic molecular linkers to form a highly connected porous network.

Catalysts based on the porous MOFs can unify the best features of homogeneous catalysts (e.g., selectivity and ease of modification) and heterogeneous catalysts (e.g., ease of purification and recyclability). The modular nature and facile tunability of the MOFs render then well-suited as heterogeneous catalysts with uniform active sites. In catalysis, the MOFs may allow for the same level of structural refinement as molecular homogeneous catalysts, while their high surface area, pore volume, and heterogeneous nature can facilitate good catalytic activity and rapid purification.

Figure 1:
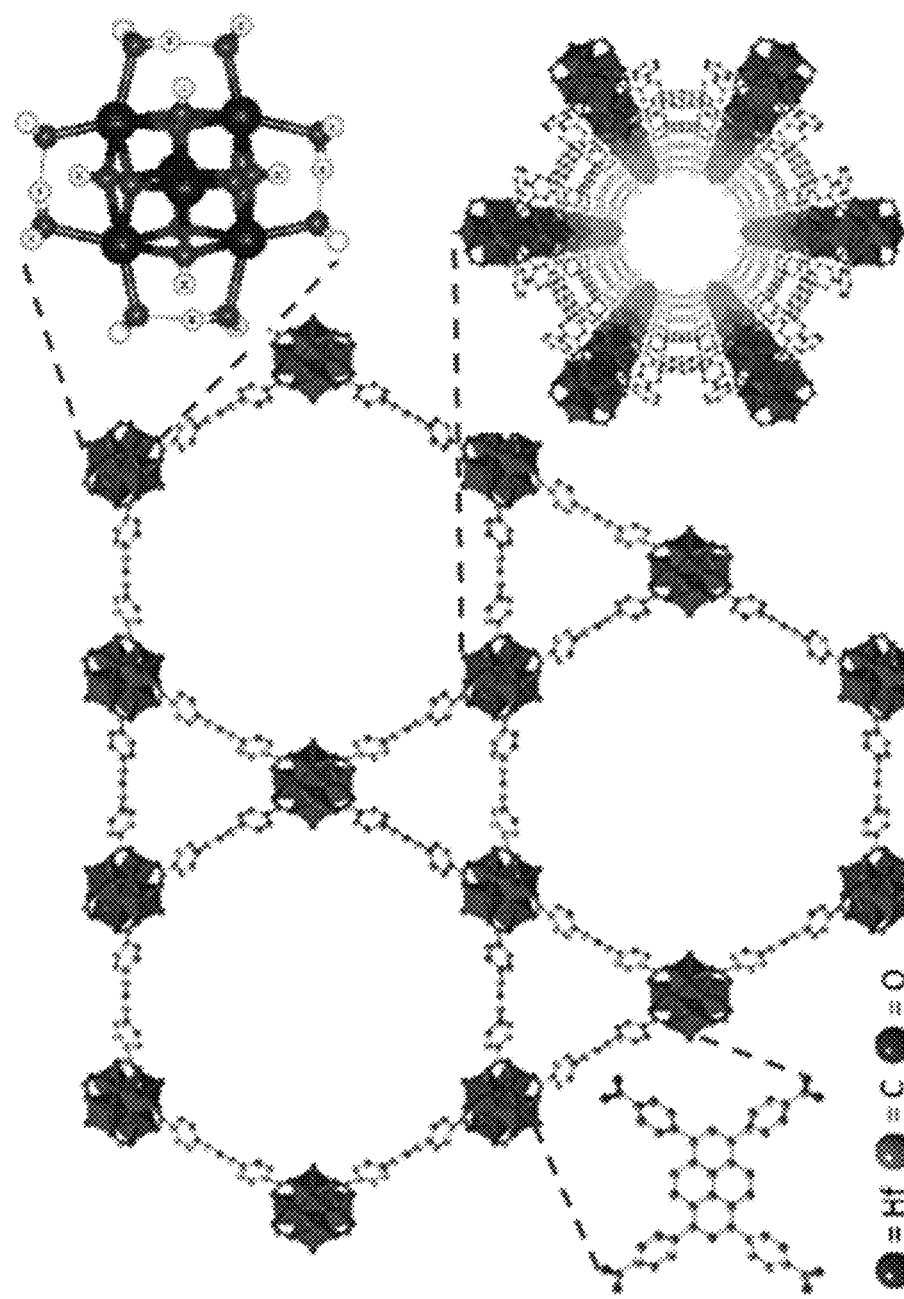
FIG. 1. Relevant structural features and representations of Hf-NU-1000. For simplicity hydrogen atoms, except for the cluster, are not shown. For clarity, the carboxylates are removed from the cluster shown in the top inset.

The MOFs comprise inorganic nodes composed of an octahedral $M_6$ cluster capped by eight $\mu_3$-ligands and having twelve octahedral edges, wherein M is Zr or Hf and the 0.3-ligands are selected from hydroxo ligands, oxo ligands or aquo ligands. Organic linkers connect the inorganic nodes. The inorganic linkers comprise 1,3,6,8-tetrakis(p-benzoic acid)pyrene (TBAPy) units, wherein eight of the twelve octahedral edges of the inorganic nodes are connected to the 1,3,6,8-tetrakis(p-benzoic acid)pyrene units. The structure of the MOFs can be represented by the formula: $M_6(\mu_3\text{-ligand})_8(OH_x)_8)(TBAPy)_2$, where M is Zr or Hf, the ligands are selected from hydroxo-, oxo- and aquo-ligands, and x is independently selected from 1 (i.e., —OH groups) or 2 (i.e., $H_2O$ groups). The structure of a polyoxohafnium cluster based MOF is shown in FIG. 1. The polyoxozirconium cluster based MOF is isostructural with the MOF shown in FIG. 1.

The MOFs may be used as nucleophilic ring-opening catalysts in various reactions. The methods for carrying out the reactions comprise the steps of combining an epoxide ring-containing molecule with a reactant in the presence of a catalytic amount of the MOF in a solution, wherein the MOF catalyzes the nucleophilic epoxide ring opening of the epoxide ring-containing molecule to provide an activated epoxide. The activated epoxide then goes on to react with the reactant to form a product molecule. The epoxide ring-containing molecule may be, for example, an aryl-substituted epoxide, such as styrene oxide, methylstyrene oxides, or derivatives thereof. Alternatively, the epoxide ring-containing molecule may be an alkyl-substituted epoxide, such as propylene oxide, ethylene oxide, or derivatives thereof.

Figure 3:
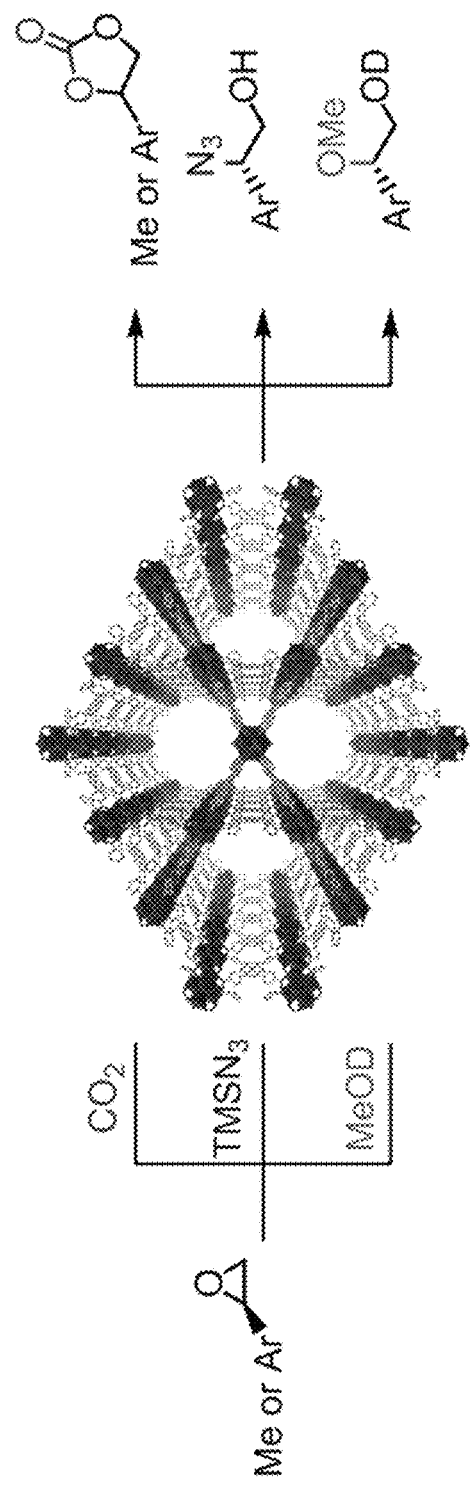
FIG. 3. Reaction schemes for the various epoxide ring-opening based reactions catalyzed by MOFs.

In some embodiments of the methods, the MOFs are used to catalyze cycloaddition reactions of $CO_2$ with epoxides to yield cyclic carbonates. This is illustrated in top reaction scheme depicted in FIG. 3. For example, the reaction of $CO_2$ with styrene oxide or propylene oxide can be catalyzed by the MOF to form the products styrene carbonate or propylene carbonate, respectively. Thus, the MOFs can be used to facilitate the chemical fixation of $CO_2$ as an inexpensive, environmentally benign, ubiquitous, and sustainable carbon source for the preparation of cyclic carbonates. In some embodiments, this is carried out under ambient conditions.

In other embodiments of the methods, the MOFs are used to catalyze solvolytic reactions and to activate epoxides for the regioselective and enantioretentive synthesis of 1,2-bifuctionalized systems. For example, the reaction of azides with epoxide ring-containing molecules can be catalyzed by the MOFs to form β-azohydrins via regioselective and enantioretentive azidolysis. This is illustrated in middle reaction scheme depicted in FIG. 3. By way of illustration, styrene oxide can be reacted with trimethylsilyl azide in the presence of a MOF to form a β-azido alcohol. Alternatively, the reaction of alcohols with epoxide ring-containing molecules can be catalyzed with the MOFs to form β-alkoxy alcohols via regioselective and enantioretentive alcoholytic epoxide ring-opening of the epoxide molecule. This is illustrated in the bottom reaction scheme depicted in FIG. 3. By way of illustration, styrene oxide can be reacted with methanol in the presence of a MOF to form β-methoxy alcohol via methanolysis.

Figure 4:
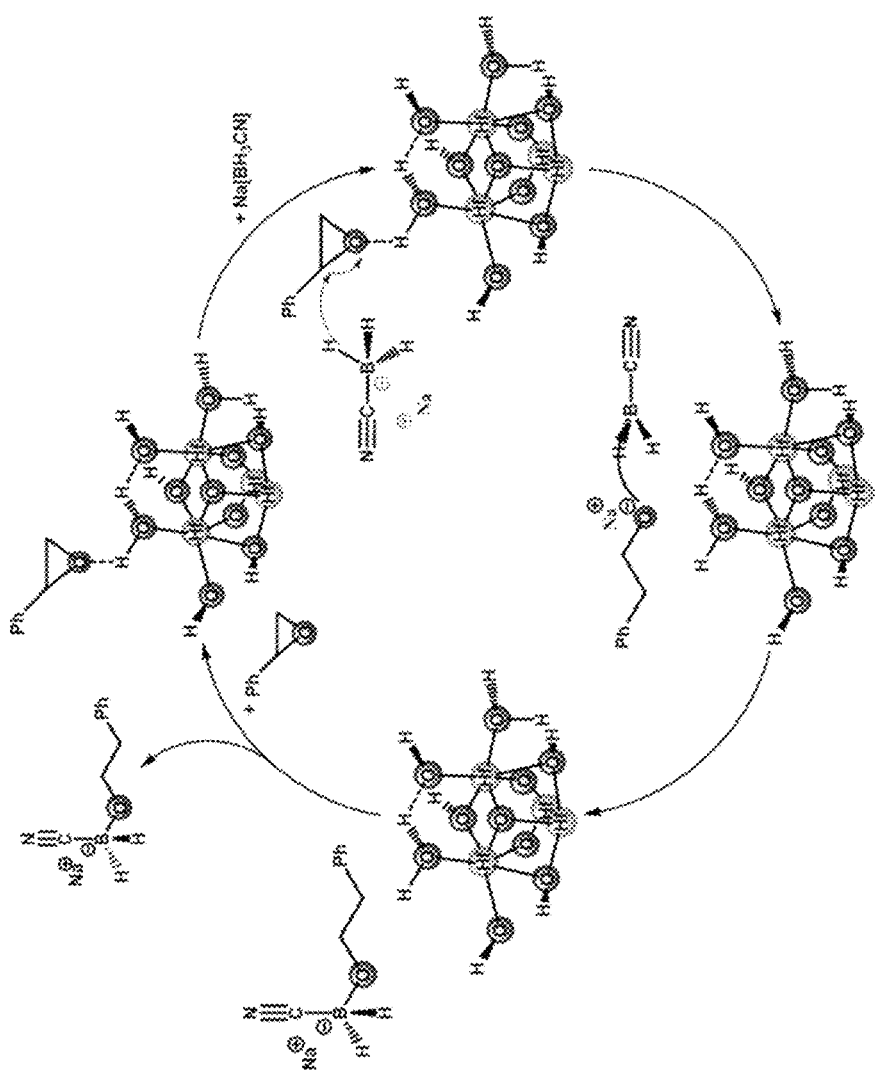
FIG. 4. Proposed catalytic cycle for ring-opening of styrene oxide with sodium cyanoborohydride, catalyzed by Hf-NU-1000. The epoxide is activated by H-bonding with the acidic protons of the $Hf_6$ core. The hydride attacks the benzylic carbon in an $S_N2$ fashion. The alkoxide then attacks $BH_2CN$ moiety. The catalytic cycle is complete when a new molecule of styrene oxide H-bonds with Hf-NU-1000. For clarity, the bottom third of the hafnium core and the ligand carboxylate groups have been omitted.

In still other embodiment of the methods, the MOFs are used to catalyze the regioselective formation of primary alcohols from epoxides and hydrides. A proposed catalytic reaction scheme for this process is depicted in FIG. 4. For example, the reaction of hydrides with epoxide ring-containing molecules can be catalyzed by the MOF to form 1° alcohols via regioselective epoxide ring-opening. By way of illustration, a hydride, such as cyanoborohydride can be reacted with styrene oxide or propylene oxide in the presence of a MOF to form 2-phenylethanol or 2-propanol, respectively.

Example 1

NU-1000 was obtained via the solvothermal reaction of $ZrCl_4$, 1,3,6,8-tetrakis(p-benzoic acid)pyrene ($H_4TBAPy$), and benzoic acid as a modulator. (Mondloch, J. E.; Bury, W.; Fairen-Jimenez, D.; Kwon, S.; DeMarco, E. J.; Weston, M. H.; Sarjeant, A. A.; Nguyen, S. T.; Stair, P. C.; Snurr, R. Q.; Farha, O. K.; Hupp, J. T. *J. Am. Chem. Soc.* 2013, 135, 10294.) The parent-framework node is composed of an octahedral $Zr_6$ cluster capped by eight bridging oxygen-containing ligands. The 3-D NU-1000 structure can be described as Kagome 2-D sheets linked by TBAPy ligands. NU-1000 shares the same topological features as MOF-545 (Morris, W.; Volosskiy, B.; Demir, S.; Gandara, F.; McGrier, P. L.; Furukawa, H.; Cascio, D.; Stoddart, J. F.; Yaghi, O. M. *Inorg. Chem.* 2012, 51, 6443) and PCN-222 (Feng, D. W.; Gu, Z. Y.; Li, J. R.; Jiang, H. L.; Wei, Z. W.; Zhou, H. C. *Angew. Chem. Int. Ed.* 2012, 51, 10307); comprising of triangular and hexagonal channels.

This example describes the preparation of an Hf-based MOF (Hf-NU-1000) with the same topology as NU-1000. To confirm that NU-1000 and Hf-NU-1000 have the same overall crystal structure, periodic density functional theory (DFT) within the Vienna ab initio simulation package (VASP) (Vermoortele, F.; Bueken, B.; Le Bars, G.; Van de Voorde, B.; Vandichel, M.; Houthoofd, K.; Vimont, A.; Daturi, M.; Waroquier, M.; Van Speybroeck, V.; Kirschhock, C.; De Vos, D. E. *J. Am. Chem. Soc.* 2013, 135, 11465) was used to optimize the ionic positions of NU-1000 starting from the validated NU-1000 X-ray diffraction data. The $Zr^{4+}$ ions were then replaced with $Hf^{4+}$ and the simulated Hf-NU-1000 structure was used to optimize the ionic positions. Comparison of the experimental and simulated PXRD patterns of Hf-NU-1000 and NU-1000 confirmed that the Hf and Zr versions of NU-1000, are indeed isostructural (FIG. 1).

The porosity of Hf-NU-1000 was studied by $N_2$ adsorption-desorption experiments at 77 K and the resulting isotherm (type IVc) yielded a Brunauer-Emmett-Teller (BET) surface area of 1780 $m^2\ g^{-1}$ and a total pore volume of 1.14 $cm^3\ g^{-1}$. DFT pore size distribution analysis revealed pore diameters of ca. 13 Å and 29 Å, assignable to the triangular micropores and hexagonal mesopores, respectively. Thermal gravimetric analysis (TGA) on the activated sample showed no major decomposition up to 500° C. Diffuse reflectance infrared Fourier transform spectroscopy (DRIFTS) confirmed the presence of —OH groups and $H_2O$ molecules in the $Hf_6$ nodes, with peaks at 3679 $cm^{-1}$ assigned to the non H-bonded —OH and bridging —OH stretches, the peak at 3678 $cm^{-1}$ assigned to the non H-bonded $H_2O$ stretch, and the peak at 2752 $cm^{-1}$ assigned to the H-bonded $H_2O$ and OH stretches.

Given the high stability, porosity, and large channels of Hf-NU-1000, its performance as an acid catalyst was investigated in the context of $CO_2$ fixation through reaction with epoxides to form cyclic carbonates under ambient conditions. As shown in Table 1 (Entry 1a), Hf-NU-1000 demonstrates highly efficient catalytic activity for the quantitative cycloaddition of styrene oxide using 1 atm of $CO_2$ gauge pressure to form styrene carbonate at room temperature (r.t.; ~23° C.). To the best of the inventors' knowledge, this is the mildest and the most efficient catalytic system for this type of reaction. Since the conversion of epoxide to carbonate is complete and quantitative, the pure product could be obtained after a simple aqueous extraction, without the need for laborious purification steps such as distillation, which can cause decomposition of the product and the formation of by-products. Under the same reaction conditions, NU-1000 was not as efficient as Hf-NU-1000. (Table 1, Entry 1b). Employing the same reaction conditions, but in the absence of catalyst, no product was obtained (Table 1, Entry 1c). The same reaction proceeds much faster at elevated temperature (55° C., 13 h) (Table 1, Entry 1d). Hf-NU-1000 was compared with reported MOFs Cr-MIL-101, MOF-5, ZIF-8, Ni(salphen)-MOF, Co-MOF-74, Mg-MOF-74, [Cu(Hip)$_2$(Bpy)]$_n$ (CHB(M)), ZIF-68, F-IRMOF-3 and MIL68(In)-NH$_2$ (Table 2, Entries 1e-n) which have also been used for the preparation of styrene carbonate, and Hf-NU-1000 clearly stands out in terms of yield and milder conditions.

TABLE 1

Comparison of cycloaddition reactions of CO$_2$ with epoxides by different MOF catalysts yielding cyclic carbonates.

| Entry | Catalyst | Subs | Prod | T [° C.] | P [atm.] | t [h] | Yield [%] |
|---|---|---|---|---|---|---|---|
| 1a[a] | Hf-NU-1000 | | | r.t. | 1 | 56 | 100[c] |
| 1b[a] | NU-1000 | | | r.t. | 1 | 56 | 46[c] |
| 1c[b] | — | | | r.t. | 1 | 56 | 0[c] |
| 1d[a] | Hf-NU-1000 | | | 55 | 1 | 13 | 100[c] |
| 1e | Cr-MIL-101[1] | | | r.t. | 8 | 48 | 95 |
| 1f | MOF-5[2] | | | 50 | 1 | 15 | 92 |
| 1g | ZIF-8[3] | | | 80 | 7 | 5 | 39 |
| 1h | Ni(sal.)-MOF[4] | styrene oxide | styrene carbonate | 80 | 20 | 4 | 81 |
| 1i | Co-MOF-74[5] | | | 100 | 20 | 4 | 96 |
| 1j | Mg-MOF-74[6] | | | 100 | 10 | 4 | 95 |
| 1k | CHB(M)[7] | | | 120 | 12 | 6 | 56 |
| 1l | ZIF-68[8] | | | 120 | 10 | 12 | 93 |
| 1m | gea-MOF-1[9] | | | 120 | 20 | 6 | 85 |
| 1n | F-IRMOF-3[10] | | | 140 | 20 | 5 | 84 |
| 1o | MIL68(In)-NH$_2$[11] | | | 150 | 8 | 8 | 71 |
| 2[a] | Hf-NU-1000 | bis-epoxide | bis-carbonate | 55 | 1 | 19 | 100[c] |
| 3a[a] | Hf-NU-1000 | | | r.t. | 1 | 26 | 100[c] |
| 3b[d] | HKUST-1[12] | | | r.t. | 1 | 48 | 49 |
| 3c[d] | MOF-505[13] | | | r.t. | 1 | 48 | 48 |
| 3d[d] | MMPF-9[14] | | | r.t. | 1 | 48 | 87 |
| 3e | MMCF-2[15] | | | r.t. | 1 | 48 | 95 |
| 3f | Cr-MIL-101[1] | propylene oxide | propylene carbonate | r.t. | 8 | 24 | 82 |
| 3g | MOF-5[2] | | | 50 | 4 | 4 | 93 |
| 3h | Ni(sal.)-MOF[4] | | | 80 | 20 | 4 | 80 |
| 3i | PCN-224(Co)[16] | | | 100 | 20 | 4 | 42 |
| 3j | CHB(M)[7] | | | 120 | 12 | 6 | 62 |
| 3k | gea-MOF-1[9] | | | 120 | 20 | 6 | 88 |
| 3l | MIXMOF[17] | | | 140 | 40[e] | 3 | 63 |

[a]Reaction conditions: epoxide (0.2 mmol), cat. (4.0 mol % of —OH active site), $n$Bu$_4$NBr (10 mol %) under 1 atm of CO$_2$ gauge pressure.
[b]The same conditions as [a], but without cat.
[c]Determined by $^1$H NMR using 1-bromo-3,5-difluorobenzene as the internal standard.
[d]Data derived from W.-Y. Gao, Y. Chen, Y. Niu, K. Williams, L. Cash, P. J. Perez, L. Wojtas, J. Cai, Y.-S. Chen, S. Ma, *Angew. Chem. Int. Ed.* 2014, 53, 2615-2619.
[e]The pressure was calculated based on Van der Waals equation.

The industrially important epoxide divinylbenzene dioxide (DVBDO) was also examined and the biscarbonated DVBDO, which could be a useful epoxy resin monomer candidate was obtained quantitatively after 19 h at 55° C. (Table 1, Entry 2). Hf-NU-1000 was also compared with other MOF materials for the conversion of propylene oxide (PO) to propylene carbonate (Table 1, Entry 3a, r.t. 26 h). Hf-NU-1000 again showed faster reaction time and higher product yield compared to the previously reported MOFs MMCF-2, PCN-224(Co), HKUST-1, MOF-505, MMPF-9, Cr-MIL-101, MOF-5, Ni(salphen)-MOF, [Cu(Hip)$_2$(Bpy)]$_n$ CHB(M) and Zn$_4$O(BDC)$_x$(ABDC)$_{3-x}$ based on MOF-5 (MIXMOF) (Table 1, Entries 3b-k). It is worth noting, PO is more studied than styrene oxide due to its higher reactivity and ease of isolation. However, as a result of its low boiling point it could easily lead to mass loss which can complicate yield calculation, thus extreme care of handling should be applied.

To confirm the heterogeneous nature of the reaction, under the same conditions as in Table 1 Entry 1a, 40 h after the outset of the reaction, the catalyst was removed and the reaction was allowed to continue. As expected, no increase in the formation of carbonate was detected. At the end of the reaction, inductively coupled plasma (ICP) analysis of the reaction mixture filtrate revealed no Hf leaching, indicating the catalytic reaction is indeed heterogeneous in nature. Additionally, in the absence of ammonium salt co-catalyst, no conversion was detected for the model reaction. Furthermore, the catalyst was reused five successive times without a significant decrease in the efficiency of the catalyst or structural deterioration based on PXRD analysis.

Next, the performance of Hf-NU-1000 in the activation of epoxides for the preparation of 1,2-bifuctionalized systems via acid-catalyzed nucleophilic ring opening was investigated. As the initial step, the focus was on the synthesis of vicinal azidohydrins which are important precursors of α-amino alcohols (known as β-blockers). Additionally, vicinal azidohydrins are present in various bioactive natural products, and in the chemistry of carbohydrates, nucleosides, lactams, and oxazolines. Although azidohydrins are generally synthesized from epoxides by the reaction with an alkali azide, this classical method is often accompanied by side reactions such as isomerization, epimerization, and rearrangement. To the best of the inventors' knowledge, there is no report of highly regioselective azidolysis of epoxides with a high yield and complete conversion of substrate. Tanabe et al. and Song et al. have studied this reaction using a series of MOFs, however, they only obtained moderate conversions and/or required stepwise postsynthetic modifications. (Tanabe, K. K.; Cohen, S. M. *Inorg. Chem.* 2010, 49, 6766; and Song, F. J.; Wang, C.; Lin, W. B. *Chem. Commun.* 2011, 47, 8256.)

Under the optimized conditions, Hf-NU-1000 catalyzed the solvolytic reaction of trimethylsilyl azide (TMS-N$_3$) with styrene oxide with high regioselectivity and complete conversion of substrate (Table 2, Entry 1). The catalyst also was reused for five successive times, and neither considerable decrease in the efficiency of the catalyst nor structural deterioration based on PXRD analysis was observed. In order to gain a better understanding of the origin of this unique regioselectivity, a few control reactions were conducted. First, hafnium$^{IV}$ oxychloride octahydrate was utilized as a Lewis acid catalyst to examine whether the origin of regioselectivity was from Hf$^{IV}$; the conversion was decreased to 75% and the co-occurrence of a side-product (30%) was observed (Table 2, Entry 2). In the case of using dehydrated Hf-NU-1000, both of the conversion (60%) and regioselectivity (85:15) were decreased (Table 2, Entry 3). Additionally, aqueous HCl (an alternative homogeneous catalysts) was used to catalyze this reaction, but it showed poor conversion (48%) and the co-occurrence of a side-product (25%) was observed (Table 2, Entry 4).

TABLE 2

Investigation of azidolysis of styrene under various conditions to form the β-azidohydrins.

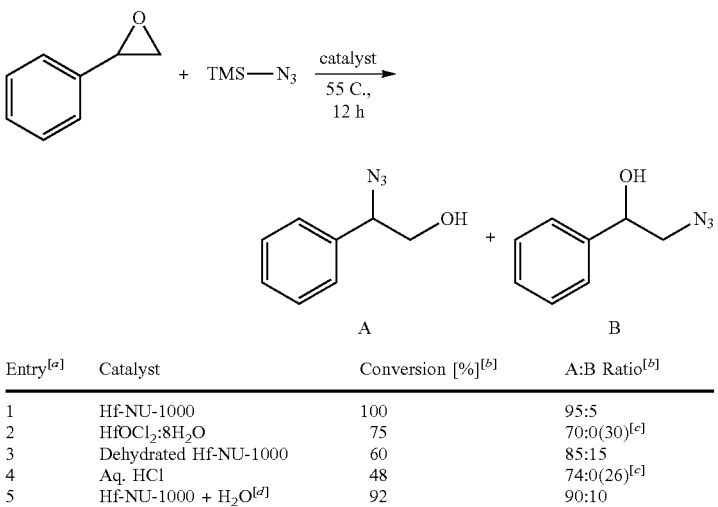

| Entry[a] | Catalyst | Conversion [%][b] | A:B Ratio[b] |
|---|---|---|---|
| 1 | Hf-NU-1000 | 100 | 95:5 |
| 2 | HfOCl$_2$:8H$_2$O | 75 | 70:0(30)[c] |
| 3 | Dehydrated Hf-NU-1000 | 60 | 85:15 |
| 4 | Aq. HCl | 48 | 74:0(26)[c] |
| 5 | Hf-NU-1000 + H$_2$O[d] | 92 | 90:10 |

[a]Reaction conditions: styrene oxide: 0.2 mmol, azidotrimethylsilane (4.0 mmol) acts also as the solvent.
[b]After work-up and determined by $^1$H NMR using 1-bromo-3,5-difluorobenzene as an internal standard.
[c]Refers to a side-product.
[d]The same mole equivalence of H$_2$O as Entry 2 was added to assess the effect of water.

Figure 2:
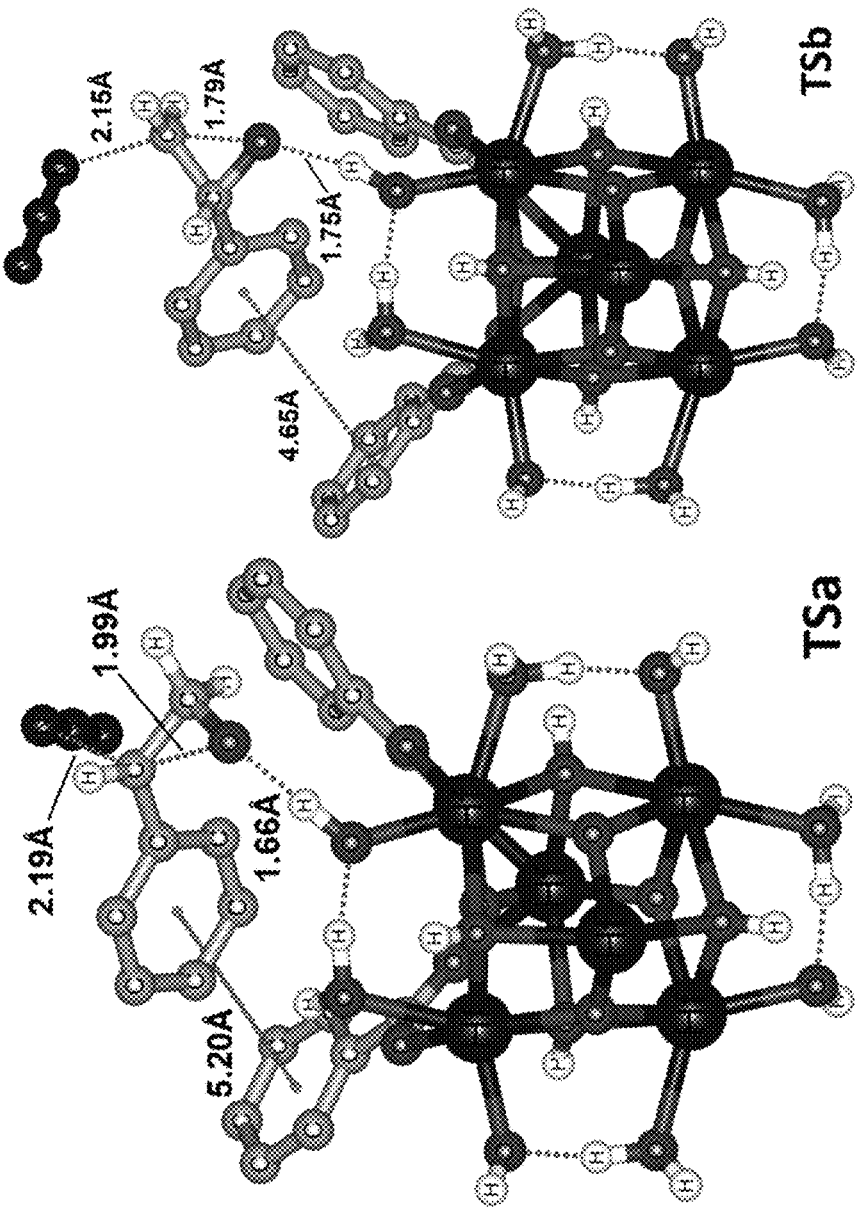
FIG. 2. Optimized geometries of the TS structures TSa and TSb for the epoxide ring-opening steps leading to the products A and B, respectively. Hydrogen atoms of the phenyl rings are removed for clarity.

In order to elucidate the mechanism of the reaction, computational modeling was used. Quantum-chemical calculations were carried out using the M06-L/def2-SVP density functional model as implemented in the Gaussian 09 program package. The SMD continuum solvent model was employed to account for solvation with TMS-N₃ as a solvent. (Marenich, A. V.; Cramer, C. J.; Truhlar, D. G. *J. Phys. Chem. B* 2009, 113, 6378.) Hf-NU-1000 serves as a proton donor in the ring opening reaction due to the presence of aqua- and OH-ligands in the Hf₆-node. The calculations showed that styrene oxide formed an association complex with the Hf₆-node via both hydrogen bonding and π-stacking interactions. The main criteria defining the reaction selectivity are the difference in the activation barriers of the ring epoxide opening step (kinetic factor), and the relative stability of the products (if the reaction operates under thermodynamic control). The optimized geometries of the transition state (TS) structures TSa (azide attack to benzylic position) and TSb (azide attack to less hindered side) leading to products A and B are depicted in FIG. 2. In both TS structures the aromatic ring of styrene oxide engages in a T-shaped π-stacking interaction with the aromatic rings of the Hf₆-node linker ligands. The calculations show that, for the reaction catalyzed by the Hf₆-node, the difference in activation free energies was 3.0 kcal/mol, while in the case of HCl the difference was about 2 kcal/mol. The difference in the free energies of the products ($\Delta_f G°$ 298(b')−$\Delta_f G°$ 298(a')) was 0.1 kcal/mol, while with HCl it was −2.3 kcal/mol. These numbers track the variations in the experimental ratios of the products A and B. To assess the effect of the predicted π-stacking interaction, propylene oxide was reacted with TMS-N₃, under the same conditions as mentioned in Table 2 for styrene oxide, and a dramatic decrease in regioselectivity was detected. In this case, a 75:25 ratio of the two regioisomers being the major product as the result of azide attack at the less hindered side was observed.

Hf-NU-1000 was then employed to catalyze alcoholytic epoxide ring-opening. The opening of epoxides with alcohols is an important transformation in the synthesis of 3-alkoxy alcohols. However, generally, the application of such reactions is limited because of the poor nucleophilicity of alcohols, which requires harsh and/or strongly acidic conditions, usually leading to the formation of a mixture of regioisomers and polymerization. Therefore, the regioselective alcoholysis of epoxides has been the subject of extensive studies. Based on the above optimized geometries of the transition states, it was speculated that the approach of methanol to hydrogen-bonded epoxide would show good stereoselection. Therefore, under optimized conditions, (+)-R-styrene epoxide was reacted with methanol in the presence of Hf-NU-1000 (4.0 mol %). The regioisomer corresponding to attack at the benzylic position was obtained with inversion of the epoxide stereogenic center selectively and in an enantioretentive fashion (Scheme 1, top). Additionally, (+)-(R)-styrene epoxide was also reacted with TMS-N₃ in the presence of Hf-NU-1000 (4.0 mol %). Again, the preferred regioisomer was obtained with inversion of the epoxide stereogenic center in an enantioretentive fashion (Scheme 1, bottom). These unique enentioretentions indicate an S_N2-type mechanism in which the carbocation is not formed as an intermediate. Hf-NU-1000, an achiral catalyst, yielded the enantiomerically pure product, which makes it promising catalyst in asymmetric catalysis on account of its simple design.

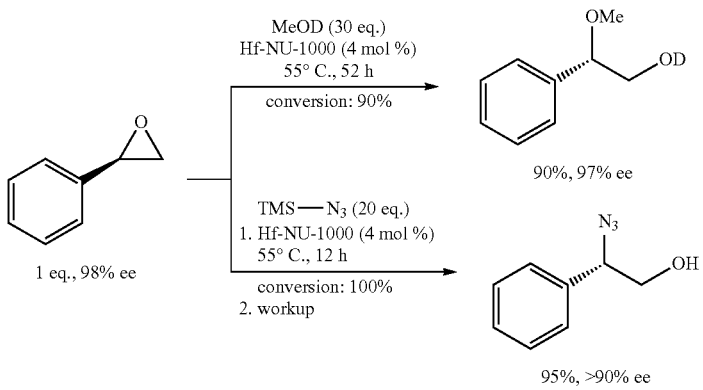

Scheme 1. Regioselective & enantioretentive methanolysis (top) and azidolysis (bottom) of styrene oxide catalyzed by Hf-NU-1000 to β-methoxy- and β-azido alcohol.

Detailed Materials and Methods for Example 1

Materials

All compounds and solvents: 1,3,6,8-Tetrabromopyrene (Aldrich, 97%), (4-(methoxycarbonyl)phenyl)boronic acid (Combi-Blocks, 98%), K₃PO₄ (Aldrich), tetrakis(triphenylphosphine) palladium(0) (Strem Chemicals, 99%), benzoic acid (Aldrich, 99.5%), HfOCl₂.8H₂O (Strem Chemicals Inc., 98+%-Hf, 1.5% Zr), styrene oxide (Aldrich, 97%), divinylbenzene dioxide (DVBDO) (The Dow Chemical Co., 96.6%, mixture of isomers), (±)-propylene oxide (Aldrich, 99.5%), tetrabutylammonium bromide (Aldrich, 99%), hydrochloric acid (Aldrich, 37%), acetone (Macron, 98%), chloroform (BDH, 99.8%), 1,4-dioxane (Aldrich, 99.8%, anhydrous), N,N-dimethylformamide (DMF) (Macron, 99.8%), tetrahydrofuran (THF) (Macron, 99.0%), (R)-(+)-styrene oxide 94%, optical purity ee: 98% (AK Scientific, Inc.), deuterated chloroform (CDCl₃-d) (Cambridge, 99.8%), deuterated dimethylsulfoxide (DMSO-d₆) (Cambridge, 99%), deuterated sulfuric acid (D₂SO₄) (Cambridge, 96-98% solution in D₂O), deuterated benzene (C₆D₆) (Aldrich, 99.6 atom % D) were used as received without further purification. For the catalytic reactions, yields were determined by ¹H NMR using 1-bromo-3,5-difluorobenzene (Mallinckrodt Chemical Co., 99.5%) as the internal standard. Chiral separation was accomplished on a Shimadzu Prominence HPLC System, using a Diacel Corporation Inc. Chiralpak® AI-3 column (3 m particle size, 4.6 mm I.D.× 250 mm) and HPLC grade solvents purchased from Aldrich (CHROMASOLV®).

Instrumentation $^1$H NMR spectra were recorded on Agilent DD2 600 MHz system with triple resonance (HCN) cold probe with z-gradient, Bruker Avance III 500 MHz system with a DCH cryo-probe and automated 400 MHz Agilent DD MR-400 system equipped with Agilent 7600 96-sample auto-sampler. Powder X-ray diffraction measurements were carried out on a Bruker MX IµS microsource with Cu Kα radiation and an Apex II CCD detector. The samples as powders were mounted either in oil on nylon loops or in capillaries sealed with wax and placed on a goniometer head. The data were collected on an area detector with rotation frames over 180° in Φ and at 2θ values of 12, 24, 36 and 48° being exposed for 10 min at each frame. Overlapping sections of data were matched, and the resulting pattern was integrated using Bruker's APEX2 phase ID program. The powder patterns were treated for amorphous background scatter. Thermogravimetric analysis (TGA) was performed on a Mettler Toledo TGA under $N_2$ flow and heated from room temperature to 700° C. (at 10° C./min). Inductively coupled plasma-optical emission spectroscopy (ICP-OES) data were collected on Varian Vista MPX instrument. Elemental analysis was performed by Galbraith Laboratories (Knoxville, Tenn.). Diffuse reflectance infrared spectra (DRIFTS) were recorded on a Nicolet 7600 FTIR spectrometer equipped with an MCT detector. The spectra were collected under $N_2$ purge. The samples were prepared by mixing with KBr in the atmosphere. KBr was utilized as the background. $N_2$ adsorption isotherms were collected on a Tristar II 3020 (Micromeritics). All the reported pressures for the cycloaddition reactions in the presented work refer to the gauge pressures. All pore size distributions were obtained using a carbon slit pore model with a $N_2$ kernel (Micromeritics).

Synthesis of 1,3,6,8-tetrakis(p-benzoic acid)pyrene (TBAPy)

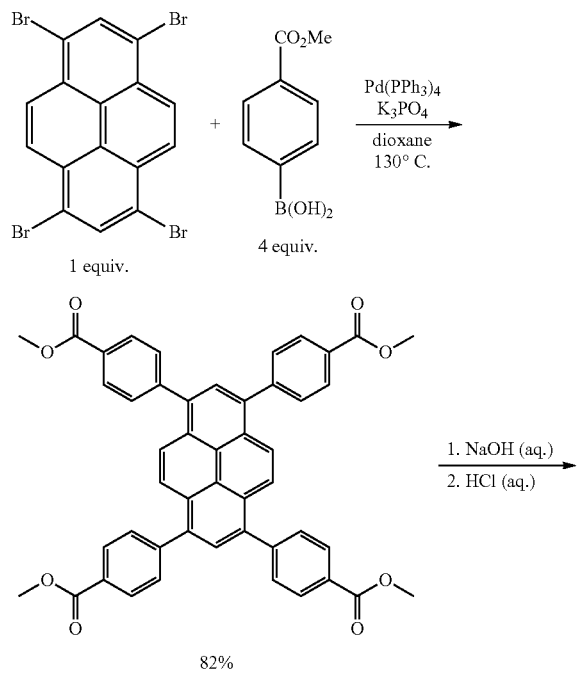

Scheme 3. Synthetic scheme and yields for H₄TBAPy.

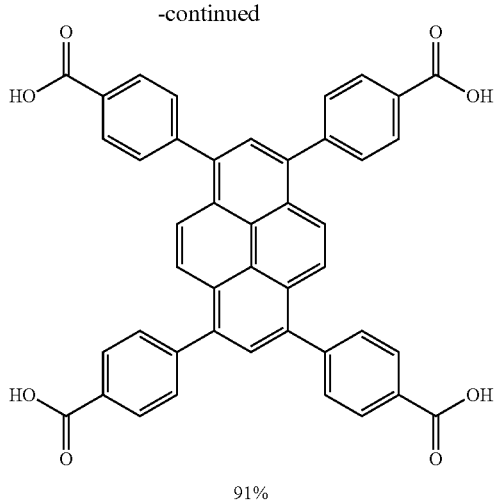

1,3,6,8-tetrakis(4-(methoxycarbonyl)phenyl)pyrene

Based on a reported procedure, a mixture of (4-(methoxycarbonyl)phenyl)boronic acid (1.040 g, 5.80 mmol), 1,3,6,8-tetrabromopyrene (0.500 g, 0.97 mmol), tetrakis(triphenylphosphine) palladium(0) (0.030 g 0.026 mmol), and potassium tribasic phosphate (1.100 g, 5.30 mmol) in dry dioxane (20 mL) was loaded (in a glovebox) into a 20 mL microwave vial (Biotage) and capped. (J. E. Mondloch, W. Bury, D. Fairen-Jimenez, S. Kwon, E. J. DeMarco, M. H. Weston, A. A. Sarjeant, S. T. Nguyen, P. C. Stair, R. Q. Snurr, O. K. Farha, J. T. Hupp, *J. Am. Chem. Soc.* 2013, 135, 10294-10297.) This mixture was stirred under argon for 72 h at 130° C. in an oil bath. The reaction mixture was evaporated to dryness and the solid residue was washed with water to remove inorganic salts. The insoluble material was extracted with chloroform (three times by 50 mL), the extract was dried over magnesium sulfate, and the solvent volume was reduced under vacuum. The residue was boiled in tetrahydrofuran for 2 h and filtered; the resulting filtrate contained mainly impurities. This procedure gave 0.58 g of 1,3,6,8-tetrakis(4-(methoxycarbonyl)phenyl)pyrene (82% yield). $^1$H NMR (CDCl$_3$-d): δ 3.99 (s, 12H), 7.75 (d, 8H), 8.01 (s, 2H), 8.15 (s, 4H), 8.23 (d, 8H).

1,3,6,8-tetrakis(p-benzoic acid)pyrene

Based on a reported procedure, to a 250 mL round bottom flask containing 0.58 g (0.78 mmol) of solid 1,3,6,8-tetrakis (4-(methoxycarbonyl)phenyl)pyrene, a solution containing 1.5 g (37.5 mmol) NaOH in 100 mL of a THF/water (ratio 1:1) mixture was added and the resultant suspension was vigorously stirred under reflux overnight. (J. E. Mondloch, W. Bury, D. Fairen-Jimenez, S. Kwon, E. J. DeMarco, M. H. Weston, A. A. Sarjeant, S. T. Nguyen, P. C. Stair, R. Q. Snurr, O. K. Farha, J. T. Hupp, *J. Am. Chem. Soc.* 2013, 135, 10294-10297.) The solvents were removed under vacuum and water was added to the residue which formed a clear yellow solution. The clear yellow solution was stirred at room temperature for 2 h and the pH value was adjusted to 1 using concentrated HCl. The resulting yellow solid was collected by filtration, and washed with water several times. The crude product was recrystallized from DMF, filtered, washed with chloroform and dried under vacuum. This gave 0.49 g (91%) of the pure product H4TBAPy. $^1$H NMR (DMSO-d$_6$): δ 7.86 (d, 8H), 8.09 (s, 2H), 8.17 (d, 8H), 8.21 (s, 4H), 13.12 (s, 4H).

Synthesis of Hf-NU-1000

500 mg of $HfOCl_2 \cdot 8H_2O$ (1.22 mmol), 10.80 g (88.4 mmol) of benzoic acid, and 32 mL of DMF were added to a 100-mL media bottle and the solids were dissolved via sonication. The resulting cloudy solution was incubated in an oven at 80° C. for 1 h, then removed from the oven and cooled to room temperature. 160 mg (234 mmol) of $H_4TBAPy$ was then added to the reaction solution and the mixture was sonicated for 10 min to yield a yellow suspension. The reaction mixture was placed in a 100° C. oven for 24 h, during which time yellow powder precipitated from the solution. After 24 h, the reaction was removed from the oven and cooled to room temperature. The solid was isolated by centrifugation, washed three times with 25 mL of DMF through repeated centrifugation and redispersion, and then soaked in 40 mL of DMF for 8 h. After 8 h, the yellow solid was isolated by centrifugation and re-suspended in 25 mL of DMF, transferred back into a 100-mL media bottle and 2.0 mL of 8 M aq. HCl were added. The reaction mixture was incubated in a 100° C. oven for 18 h, then removed from the oven and cooled to room temperature. The solid was isolated by centrifugation, washed three times with 25 mL of DMF, washed three times with 40 mL of acetone, and then soaked in 40 mL of acetone for 18 h. The solid was activated at 120° C. under vacuum for 18 h. Yield: 232 mg (73% yield). Elemental analysis calculated for $Hf_6(OH)_{16}(TBAPy)_2$ (%): C, 39.14; H, 2.24; Hf, 39.66. Found (1): C, 39.97; H, 1.93; Hf, 34.9. (2) C, 40.02; H, 1.88; Hf, 34.9.

Periodic DFT for Optimization of Hf-NU-1000 Ionic Positions

The starting structure for the geometry relaxation of Hf-NU-1000 was made by optimizing the structure of NU-1000 from validated X-Ray diffraction data, replacing the $Zr^{4+}$ cations with $Hf^{4+}$, and re-optimizing the structure with the same criteria. A 558 atom unit cell with P1 space group symmetry was used. Both the NU-1000 and Hf-NU-1000 structures were optimized with periodic density functional theory (DFT) as implemented in the Vienna ab initio simulation package (VASP) (G. Kresse, J. Hafner, *Phys. Rev. B, PRB* 1993, 47, 558-561; G. Kresse, J. Hafner, *Phys. Rev. B, PRB* 1994, 49, 14251-14269; and G. Kresse, J. Furthmuller, *Comp. Mater. Sci.* 1996, 6, 15-50; G. Kresse, J. Furthmuller, *Phys. Rev. B* 1996, 54, 11169-11186) employing the Perdew-Burke-Emzerhof (PBE) generalized gradient approximation exchange-correlation functional. (J. P. Perdew, K. Burke, M. Emzerhof, *Phys. Rev. Lett.* 1996, 77, 3865-3868.) Projector-augmented wave potentials were used to describe the interaction between the core and valence electrons. (P. E. Blochl, *Phys. Rev. B* 1994, 50, 17953-17979; and G. Kresse, D. Joubert, *Phys. Rev. B* 1999, 59, 1758-1775.) An energy cutoff of 520 eV was used and the integration over the irreducible Brillouin zone was performed with the gamma point. The energy and force convergence thresholds were $10^{-5}$ Å and 0.05 eV/Å, respectively.

General Procedure for the Cycloaddition Reaction of Epoxides with $CO_2$

The corresponding epoxide (0.2 mmol) as mentioned in Table 1, tetrabutylammonium bromide (6.5 mg, 0.02 mmol) pre-dissolved in 400 μL of acetonitrile and Hf-NU-1000 (4.0 mol %; 5.6 mg, equivalent to 0.008 mmol —OH as the catalytic active site considering 2700.36 gr $mol^{-1}$ ($Hf_6(\mu_3-O)_4(\mu_3-OH)_4(OH)_4(OH_2)_4(TBAPy)_2$) as the molecular weight of MOF unit with four catalytically active —OH groups) were added to an autoclave reactor, which had previously been dried for 6 h at 80° C. The autoclave reactor was vacuumed, purged with $CO_2$, and then placed under a constant pressure of carbon dioxide under 5 atm for 15 min to allow the system to equilibrate. Then the pressure was reduced to 1 atm of gauge pressure and the vessel was set at the temperature and to amount of time indicated in Table 1 during which it was shaken frequently. At the end of the reaction, the reactor was placed in an ice bath for 10 min and then opened. After catalyst separation by centrifugation, a small aliquot of the supernatant reaction mixture was taken to be analyzed by $^1H$ NMR to calculate the conversion and the yield of the reaction. For the recycling experiment, the recovered catalyst was washed with acetonitrile and centrifuged and the supernatant solution was decanted. This process was repeated for three times and then the dried catalyst was reused for the next cycle.

General Procedure for the Styrene Oxide Azidolysis

Styrene oxide (22 μL, 0.2 mmol), azidotrimethylsilane (530 μL, 4 mmol) and catalyst as indicated in Table 2 (4.0 mol %; (5.6 mg, equivalent to 0.008 mmol —OH as the catalytic active site considering 2700.36 g $mol^{-1}$ ($Hf_6(\mu_3-O)_4(\mu_3-OH)_4(OH)_4(OH_2)_4(TBAPy)_2$)) were added to a 1.5 ml micro-centrifuge tube which had previously been dried for 6 h at 60° C. and then sealed. The vial was placed in a thermo-shaker at 55° C. for 12 h, then the vial was cooled to room temperature and opened. After catalyst separation by centrifugation, a small aliquot of the supernatant reaction mixture was taken to be analyzed by $^1H$ NMR to calculate the conversion, regioselectivity and the yield of the reaction. For the recycling experiment, the recovered catalyst was washed with acetonitrile and centrifuged and the supernatant solution was decanted. This process was repeated for three times and then the dried catalyst was kept in a vacuum oven at 80° C. before reuse for the next cycle. Caution: Azidotrimethylsilane ($TMS-N_3$) is incompatible with moisture, oxidizing agents, and acids. It is easily decomposed to other compounds e.g. hydrolyzed to hydrazoic acid (hydrogen azide) which is an extremely toxic and explosive material. Therefore, the safety regulations for this reaction must be strictly followed.

To probe the reaction mechanism, the nucleophilic epoxide opening reaction was performed using racemic styrene oxide and enantio-enchirched stryene oxide in separate reactions. Starting form a near 1:1 (97:100) mixture of the styrene oxide enationmers, a near racemic mixture (95:100) of the two enantiomers of the product was formed. This comes are no surprise as no additional chiral information is imparted by the catalysts. When the enantio-enriched (R)-(+)-styrene oxide (100:1) is used however, high retention of the enantio-purity (ca. 100:9) of the product (after overnight stirring in MeOH and $K_2CO_3$ to remove the initially formed TMS ether) is observed by HPLC (85% Hex/IPA, 1 mL/min, Chiralpak® AI-3 column, 215 nm, baseline separation could not be achieved). The Hf-NU-1000 catalyzed $TMSN_3$ of styrene oxide seems to undergo an $S_N2$-type mechanism with inversion of the epoxide stereogenic center. The racemic terminal alcohol product (2-azido-2-phenylethan-1-ol) after the same basic workup procedure as mentioned above was isolated by column chromatography (silica, 0 to 40% EA/Hex, CAM stain). $^1H$ NMR (500 MHz, $CDCl_3$): δ 7.45-7.29 (m, 5H), 4.70-4.66 (m, 1H), 3.74 (ddd, J=7.0, 5.7, 1.1 Hz, 2H), 1.87 (dd, J=7.1, 6.0 Hz, 1H). $^{13}C$ NMR (126 MHz, $CDCl_3$) δ 136.38, 129.12, 128.91, 127.31, 68.04, 66.68.

Methanolysis of Styrene Oxide Catalyzed by Hf-NU-1000

Styrene oxide (22 μL, 0.2 mmol), deuterated methanol (243 μL, 6 mmol) and Hf-NU-1000 (4.0 mol %; (5.6 mg, equivalent to 0.008 mmol —OH as the catalytic active site considering 2700.36 gr $mol^{-1}$ ($Hf_6(3-O)_4(3-OH)_4(OH)_4(OH_2)_4(TBAPy)_2$)) were added to a 1 mL micro-centrifuge tube which had previously been dried for 6 h at 60° C. and then sealed. Then the vial was placed in a thermo-shaker at 55° C. for 52 h. Then at the end of the reaction, the vial was cooled to room temperature and opened. After catalyst separation by centrifugation, a small aliquot of the supernatant reaction mixture was taken to be analyzed by $^1$H NMR to calculate the conversion, regioselectivity and the yield of the reaction. (B. H. Kim, F. Y. Piao, E. J. Lee, J. S. Kim, Y. M. Jun, B. M. Lee, *Bull. Korean Chem. Soc.* 2004, 25, 881-888.) To probe the reaction mechanism, the menthanolysis reaction was performed using racemic stryrene oxide and enantio-enchirched in separate reactions. Starting form a near 1:1 (98:100) mixture of the styrene oxide enationmers, a near racemic mixture (98:100) of the two enantiomers of the product was formed. When the enantio-enriched (R)-(+)-styrene oxide (100:1) is used however, essentially complete retention of the enantio-purity (100:2) of the product is observed by HPLC using chiral column (95% Hex/IPA, 1 mL/min, Chiralpak® AI-3 column, 215 nm) The Hf-NU-1000 catalyzed methanolysis of styrene oxide seems to undergo an $S_N2$-type mechanism with complete inversion of the epoxide stereo center. The enantio-enriched product was isolated by column chromatography (silica, 0 to 20% EA/Hex, CAM stain). $^1$H NMR (500 MHz, CDCl$_3$): δ 7.40-7.28 (m, 5H), 4.29 (dd, J=8.4, 3.8 Hz, 1H), 3.74-3.57 (m, 2H), 2.22 (dd, J=9.4, 3.5 Hz, 1H). In order to determine the absolute configuration of enantio-enriched product, we reacted the (R)-(+)-styrene oxide with MeOH and then after purification of the product using HPLC with chiral column, the enantioretained product was analyzed by $^1$HNMR. $[\alpha]_D^{20}$=+98° (c=0.1, CHCl$_3$); $^1$H NMR (500 MHz, CDCl$_3$): δ 7.40-7.29 (m, 5H), 4.31 (dd, J=8.5, 3.9 Hz, 1H), 3.74-3.57 (m, 2H), 3.31 (s, 3H), 2.27-2.17 (m, 1H).

Synthesis and Characterization of Dehydrated Hf-NU-1000

Dehydrating the node was performed by activating Hf-NU-1000 under dynamic vacuum at 320° C. for 16 hrs (Scheme 4).

Scheme 4. Dehydration of HF-NU-1000 at elevated temperatures under vacuum. TBAPy ligands are not shown for clarity.

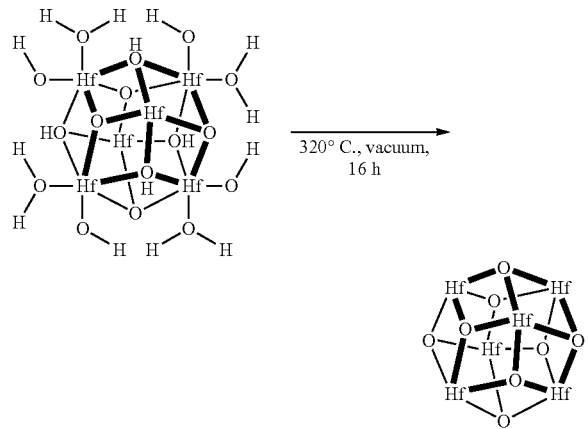

DRIFTS data for the dehydrated sample seemed to reflect loss of bound OH— and H$_2$O— groups as evidenced by the loss of signals at 3678-9 and at 2752 cm$^{-1}$.

N$_2$ adsorption-desorption experiments at 77 K for the dehydrated Hf-NU-1000 material indicated a loss of surface area and a decrease in total pore volume compared to the parent material: 930 m$^2$ g$^{-1}$ and 0.54 cm$^3$ g$^{-1}$ compared to 1780 m$^2$ g$^{-1}$ and 1.14 cm$^3$ g$^{-1}$. N$_2$ isotherms for the parent material (Hf-NU-1000) and the dehydrated material were obtained.

Example 2

Since Hf-NU-1000 acted as such a remarkable catalyst for regioselective ring-openings of epoxides with other mentioned nucleophiles, the use of Hf-NU-1000 as a catalyst to ring-open epoxides with hydrides to form 10 alcohols was investigated. Since a strong hydride would preferentially react with the acidic protons on the Hf$_6$ node, a mild hydride reagent was used to prevent non-productive formation of hydrogen. Unlike other more reactive hydrides, cyanoborohydride is stable in water at pH 7 and above, but is unreactive toward epoxides. Indeed, ring-opening of epoxides with cyanoborohydride has been carried out at low pHs (pH 3-4), by the addition of BF$_3$.etherate, ZSM-5, or by carrying out the reaction in neat acetic acid. Therefore sodium cyanoborohydride was selected as the hydride source for the ring-opening of styrene oxide. Combining four equivalents of sodium cyanoborohydride with styrene oxide at room temperature in the presence of a catalytic amount (10 mol. %) of Hf-NU-1000 produces the anti-Markovnikov product, 2-phenylenthanol, in 60% yield with over 98% selectivity (Table 3, Entry 1). (See FIG. 4 for a proposed mechanism). In the absence of Hf-NU-1000, no product was obtained (Table 3, Entry 2) indicating that Hf-NU-1000 was a necessary component of the reaction. The catalyst was reused three times without decrease in activity or loss of crystallinity as shown by powder X-ray diffraction (PXRD) measurements. To gauge the importance of the Brønsted acid sites in this reaction, a dehydrated form of the MOF, Hf-NU-1000-dehydrated (Table 3, Entry 3) was investigated. The dehydrated MOF was structurally identical to Hf-NU-1000 with the exception that there were no metal bound H$_2$O or OH molecules; only linker carboxylate groups and bridging oxo ligands were found at the Hf core. With the dehydrated MOF as the candidate catalyst, no conversion of styrene oxide was obtained, thereby illustrating the importance of Brønsted acid sites for activation of cyanoborohydride.

Scheme 2. Ring-opening of styrene oxide (top) and propylene oxide (bottom) catalyzed by Hf-NU-1000.

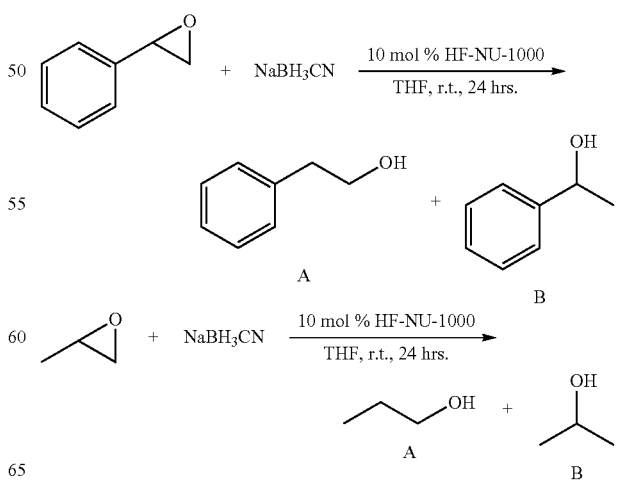

TABLE 3

Results from the Hf-NU-1000 catalyzed reactions of epoxides with various hydride sources.

| Entry[a] | Catalyst | Hydride | Substrate | Product Yield (A:B) |
|---|---|---|---|---|
| 1 | Hf-NU-1000 | NaBH$_3$CN | Styrene oxide | 60% (98:2)[d] |
| 2 | — | NaBH$_3$CN | Styrene oxide | 0%[d] |
| 3 | Hf-NU-1000-dehydrated[b] | NaBH$_3$CN | Styrene oxide | 0%[d] |
| 4[c] | Hf-NU-1000 | NaBH$_3$CN | Styrene oxide | 40% (48:52)[e] |
| 5 | Hf-NU-1000 | NaBH$_3$CN | Propylene oxide | 65% (5:95)[d] |
| 6 | — | NaBH$_3$CN | Propylene oxide | 0%[d] |

[a]General reaction conditions: 0.2 mmol substrate, 0.8 mmol. Hydride, and 0.02 mmol catalyst were stirred for 24 h. at room temp. Under a N$_2$ atmosphere in 1.9 mL dry THF.
[c]Carried out in refluxing tetrahydrofuran.
[d]Determined by $^1$HNMR
[e]Determined by GC-TOF.

A dramatic loss in both yield and selectivity occurred when the reaction was carried out in refluxing tetrahydrofuran (Table 4, Entry 4). This loss can be attributed to the deprotonation of Hf-bound acid sites by the hydride to generate H$_2$. Therefore, a $^1$H NMR experiment was conducted to assess the stability of Hf-NU-1000 under conditions that simulated reaction conditions in the presence of sodium cyanoborohydride, both at room temperature and at elevated temperatures. Under a N$_2$ atmosphere, a J. Young NMR tube was loaded with Hf-NU-1000 and sodium cyanoborohydride. Tetrahydrofuran-d$_4$ was added and the NMR tube was agitated to facilitate mixing and was left to stand for 24 h. An NMR spectrum was recorded and a small peak was observed at δ=4.5 ppm which corresponds to molecular hydrogen. The same sample was heated for 24 h. at 60° C. and another NMR spectrum was recorded using the same parameters as the room temperature spectrum. The relative peak integration at δ=4.53 was larger at elevated temperature which supports the hypothesis that deprotonation of Hf-NU-1000 occurred at elevated temperatures.

The ring-opening of propylene oxide (Table 3, Entries 5 and 6) was also investigated. A yield similar to that for styrene oxide was obtained for propylene oxide, but the regioselectivity of the reaction was reversed, with 2-propanol as the only product. Based on literature precedent and the results with styrene oxide, it was expected instead to see 1-propanol as the dominant product. (Hutchins, R. O.; Taffer, I. M.; Burgoyne, W. *J. Org. Chem.*, 46, 5214-5215 (1981).) This is an intriguing result since cyanoborohydride is generally unreactive to with epoxides; Hf-NU-1000 clearly was required for the ring opening to occur.

Detailed Materials and Methods for Example 2

Materials and Methods.

All manipulations of air-sensitive materials were performed with rigorous exclusion of oxygen and moisture in oven-dried Schlenk glassware on a dual manifold Schlenk line under N$_2$. Tetrahydrofuran used for catalytic experiments was purified according to the method reported by Grubbs. (Pangbom, A. B.; Giardello, M. A.; Grubbs, R. H.; Rosen, R. K.; Timmers, F. *J. Organometallics*, 15, 1518-1520 (1996).) NMR samples recorded in tetrahydrofuran-d$_4$ (Cambridge Isotope Laboratories, 99+atom % D) were prepared from fresh ampules. Chloroform-d$_1$ (Cambridge Isotope Laboratories, 99+atom % D) and methanol-d$_4$ (Cambridge Isotope Laboratories, 99+ atom % D) were used as received. Sodium cyanoborohydride (Aldrich, 95%), tetrabutylammonium borohydride (Aldrich, 98%) HfOCl$_2$.8H$_2$O (Strem Chemicals Inc., 98+%), styrene oxide (Aldrich, 97%), (±)-propylene oxide (Aldrich, 95%), bromocresol green (Acros, 95%), acetic acid (Aldrich, 99.7%). Hf-NU-1000 was prepared according to literature procedure, and Hf-NU-1000-dehydrated was prepared by adapting literature procedure. (Valenzano, L.; Civalleri, B.; Chavan, S.; Bordiga, S.; Nilsen, M. H.; Jakobsen, S.; Lillerud, K. P.; Lamberti, C. *Chemistry of Materials*, 23, 1700-1718 (2011).)

Physical and Analytical Measurements.

NMR spectra were recorded on Varian UNITY INOVA-400 (400 MHz, $^1$H; 100 MHz, $^{13}$C), Varian INOVA 400 (400 MHz, $^1$H; 100 MHz, $^{13}$C), Varian INOVA 500 (500 MHz, $^1$H), Bruker AVANCE III 500 (500 MHz, $^1$H; 125 MHz, $^{13}$C) NMR spectrometers. Chemical shifts (δ) for $^1$H and $^{13}$C are referenced to TMS, internal solvent resonances relative to TMS. GC-TOF data were recorded on a Waters Micromass GCT Premier time-of-flight GC mass spectrometer. Powder X-ray diffraction measurements were recorded on a Rigaku SmartLab Thin-film Diffraction Workstation with 9 kW copper rotating anode x-ray source was coupled to a multilayer optic.

Representative Procedure for Ring-Opening of Styrene Oxide with Sodium Cyanoborohydride and Hf-NU-1000.

In a Schlenk flask equipped with stir bar and septa was charged with Hf-NU-1000 (49 mg, 0.02 mmol), the flask was evacuated and backfilled three times before adding dry tetrahydrofuran (1.9 mL), styrene oxide (24 µL, 0.2 mmol), and sodium cyanoborohydride (39 mg, 0.65 mmol). The reaction was allowed to stir for 24 hours before the solvent was removed in vacuo. Dichloromethane (10 mL) was added to the residue before 1 M HCl (1 mL) was added and stirred for 20 minutes (Caution! This liberates hydrogen cyanide. Should trap HCN by bubbling reaction gas through KOH solution). The biphasic solution was stirred for ~30 minutes before adding a saturated sodium carbonate solution until basic and then stirred for another 30 minutes. The organic portion was separated from the aqueous and the aqueous portion was extracted with dichloromethane (3×10 mL portions). The organics were combined and washed with brine (5 mL) and dried over magnesium sulfate before the solution was transferred to a flask and the solvent removed in vacuo. The crude product was purified by column chromatography eluting with 25% dichloromethane in hexanes followed by 20% ethyl acetate in hexanes (~15 mg, 0.13 mmol.); yield: 63%. $^1$H NMR (CDCl$_3$): 7.2-7.5 (m, Ar-H, 5H), 3.75 (t, —CH$_2$—, 2H, J$_{HH}$=6.70 Hz), 2.77 (t, —CH$_2$—, 2H, J$_{HH}$=6.70 Hz), 2.01 (s, OH, 1H).

Qualitative Colorimetric Reactions Using Bromocresol Green.

The reaction was prepared as above except a very small amount of bromocresol green was added to the reaction.

Reaction of (±)-Propylene Oxide.

A 25 mL round bottom flask equipped with stir bar and septa was charged with Hf-NU-1000 (5.4 mg, 0.002 mmol). The round bottom was sparged with N$_2$ gas before tetrahydrofuran (1.9 mL), (±)-propylene oxide (0.024 mL, 0.02 mmol), and sodium cyanoborohydride (0.08 mmol, 5 mg) were added. The septa was replaced with a stopper and the reaction was allowed to stir for 24 hours. The reaction solution was transferred via pipette to a J. Young NMR tube. The round bottom was rinsed with MeOH-d$_4$ which was added to the NMR tube. Yield: ~65%.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

REFERENCES

[1] a) O. V. Zalomaeva, N. V. Maksimchuk, A. M. Chibiryaev, K. A. Kovalenko, V. P. Fedin, B. S. Balzhinimaev, *J. Energy Chem.* 2013, 22, 130-135; b) O. V. Zalomaeva, A. M. Chibiryaev, K. A. Kovalenko, O. A. Kholdeeva, B. S. Balzhinimaev, V. P. Fedin, *J. Catal.* 2013, 298, 179-185.
[2] J. L. Song, Z. F. Zhang, S. Q. Hu, T. B. Wu, T. Jiang, B. X. Han, *Green Chem.* 2009, 11, 1031-1036.
[3] M. Q. Zhu, D. Srinivas, S. Bhogeswararao, P. Ratnasamy, M. A. Carreon, *Catal. Commun.* 2013, 32, 36-40.
[4] Y. W. Ren, Y. C. Shi, J. X. Chen, S. R. Yang, C. R. Qi, H. F. Jiang, *RSC Adv.* 2013, 3, 2167-2170.
[5] H. Y. Cho, D. A. Yang, J. Kim, S. Y. Jeong, W. S. Ahn, *Catal. Today* 2012, 185, 35-40.
[6] D. A. Yang, H. Y. Cho, J. Kim, S. T. Yang, W. S. Ahn, *Energy Environ. Sci.* 2012, 5, 6465-6473.
[7] A. C. Kathalikkattil, D. W. Kim, J. Tharun, H. G. Soek, R. Roshan, D. W. Park, *Green Chem.* 2014, 16, 1607-1616.
[8] L. Yang, L. Yu, G. Diao, M. Sun, G. Cheng, S. Chen, *J. Mol. Catal. A: Chem.* 2014, 392, 278-283.
[9] V. Guillerm, L. J. Weselinski, Y. Belmabkhout, A. J. Cairns, V. D'Elia, L. Wojtas, K. Adil, M. Eddaoudi, *Nat. Chem.* 2014, 6, 673-680.
[10] X. Zhou, Y. Zhang, X. G. Yang, L. Z. Zhao, G. Y. Wang, *J. Mol. Catal. A: Chem.* 2012, 361, 12-16.
[11] T. Lescouet, C. Chizallet, D. Farrusseng, *ChemCatChem* 2012, 4, 1725-1728.
[12] S. S. Y. Chui, S. M. F. Lo, J. P. H. Charmant, A. G. Orpen, I. D. Williams, *Science* 1999, 283, 1148-1150.
[13] B. L. Chen, N. W. Ockwig, A. R. Millward, D. S. Contreras, O. M. Yaghi, *Angew. Chem. Int. Ed.* 2005, 44, 4745-4749.
[14] W.-Y. Gao, L. Wojtas, S. Ma, *Chem. Commun.* 2014, 50, 5316-5318.
[15] W.-Y. Gao, Y. Chen, Y. Niu, K. Williams, L. Cash, P. J. Perez, L. Wojtas, J. Cai, Y.-S. Chen, S. Ma, *Angew. Chem. Int. Ed.* 2014, 53, 2615-2619.
[16] D. W. Feng, W. C. Chung, Z. W. Wei, Z. Y. Gu, H. L. Jiang, Y. P. Chen, D. J. Darensbourg, H. C. Zhou, *J. Am. Chem. Soc.* 2013, 135, 17105-17110.
[17] W. Kleist, F. Jutz, M. Maciejewski, A. Baiker, *Eur. J. Inorg. Chem.* 2009, 3552-3561.

What is claimed is:

1. A metal-organic framework comprising:
   inorganic nodes that comprise an octahedral $Hf_6$ cluster capped by eight $\mu_3$-ligands and having twelve octahedral edges, wherein the $\mu_3$-ligands are hydroxo ligands, oxo ligands or aquo ligands; and
   organic linkers connecting the organic nodes, the organic linkers comprising 1,3,6,8-tetrakis(p-benzoic acid) pyrene units; wherein eight of the twelve octahedral edges of the inorganic nodes are connected to the 1,3,6,8-tetrakis(p-benzoic acid)pyrene units.
2. The metal-organic framework of claim 1, wherein the $\mu_3$-ligands comprise four hydroxo ligands and four oxo ligands.

* * * * *